US008226936B2

(12) United States Patent
Stroeman

(10) Patent No.: US 8,226,936 B2
(45) Date of Patent: Jul. 24, 2012

(54) TETRACYCLINE-SENSITIVE BIFIDOBACTERIA STRAINS

(75) Inventor: Per Stroeman, Naerum (DK)

(73) Assignee: CHR-Hansen A/S, Horsholm (DK)

( * ) Notice: Subject to any disclaimer, the term of this patent is extended or adjusted under 35 U.S.C. 154(b) by 320 days.

(21) Appl. No.: 12/447,572

(22) PCT Filed: Nov. 2, 2007

(86) PCT No.: PCT/EP2007/061828
§ 371 (c)(1),
(2), (4) Date: May 8, 2009

(87) PCT Pub. No.: WO2008/058854
PCT Pub. Date: May 22, 2008

(65) Prior Publication Data
US 2010/0129322 A1    May 27, 2010

(30) Foreign Application Priority Data
Nov. 15, 2006 (EP) ..................... 06023721

(51) Int. Cl.
*A01N 63/00* (2006.01)
*C12N 1/10* (2006.01)
(52) U.S. Cl. .................. 424/93.4; 424/93.45; 435/252.1
(58) Field of Classification Search ................ 424/93.4, 424/93.45; 435/252.1
See application file for complete search history.

(56) References Cited

U.S. PATENT DOCUMENTS
6,379,663 B1    4/2002    Gill et al.

FOREIGN PATENT DOCUMENTS
| EP | 0 157 071 B1 | 10/1985 |
|----|---|---|
| EP | 0 768 375 B2 | 10/1998 |
| EP | 1533382 A1 | 5/2005 |
| EP | 1724340 B1 | 2/2009 |
| WO | WO 01/97822 A1 | 12/2001 |
| WO | WO 03/099037 A1 | 12/2003 |
| WO | WO 2006/119780 A2 | 11/2006 |

OTHER PUBLICATIONS

Leon Lachman, Ph.D. et al., The Theory and Practice of Industrial Pharmacy, Third Edition, Lea & Febiger, 1986, Philadelphia, PA.
Teresa M. Barbosa et al., "Evidence for recent intergeneric transfer of a new tetracycline resistance gene, *tet*(W), isolated from *Butyriyibrio fibrisolvens*, and the occurrence of *tet*(O) in ruminal bacteria", Environmental Microbiology (1999) 1(1), pp. 53-64.
Stephen J. Billington et al., "Widespread Distribution of a Tet W Determinant among Tetracycline-Resistant Isolates of the Animal Pathogen *Arcanobacterium pyogenes*", Antimicrobial Agents and Chemotherapy, vol. 46, No. 5, May 2002, pp. 1281-1287.
Ian Chopra et al., "Tetracycline Antibiotics: Mode of Action, Applications, Molecular Biology, and Epidemiology of Bacterial Resistance", Microbiology and Molecular Biology Reviews, vol. 65, No. 2, Jun. 2001, pp. 232-260.
J.C. De Man et al., "A Medium for the Cultivation of *Lactobacilla* ", J. Appl. Bacteriol. 23:130-135.
Lydia Hung et al., "Megabase DNA Analysis: Chromosomal DNA Preparation, Restriction, and Pulsed-Field Electrophoresis", Promega Notes, No. 24, Apr. 1990, 3 pgs.
Opinion of the Scientific Panel on Additives and Products or Substances Used in Animal Feed on the Updating of the Criteria Used in the Assessment of Bacteria for Resistance to Antibiotics of Human or Veterinary Importance, the EFSA Journal (2005) 223, 1-12.
Guidelines for the Evaluation of Probiotics in Food—Report of a Joint FAO/WHO Working Group on Drafting Guidelines for the Evaluation of Probiotics in Food, World Health Organization, London Onario, Canada, 2002, pp. 1-11.
Morten Danielsen et al., "Susceptibility of *Lactobacillus* spp. To antimicrobial agents", International Journal of Food Microbiology 82 (2003) 1-11.
Michael A. Innis et al., "1 — Optimization of PCRs", PCR Protocols a Guide to Methods and Applications, 1990, pp. 3-12.
J.S. Zhou et al., "Antibiotic susceptibility profiles of new probiotic *Lactobacillus* and *Bifidobacterium* strains", International Journal of Food Microbiology, 98 (2005) 211-217.
S. Laulund, "Chapter 10 Commercial Aspects of Formulation, Production and Marketing of Probiotic Products", Formulation, Production and Marketing of Probiotic Products, Human Health: The Contribution of Microorganisms, (1994) pp. 159-173.
Liesbeth Masco et al., "Polyphasic taxonomic analysis of *Bifidobacterium animalis* and *Bifidobacterium lactis* reveals relatedness at the subspecies level: reclassification of *Bifidobacterium animalis* as *Bifidobacterium animalis* subsp. *Animalis* subsp. nov. and *Bifidobacterium lactis* as *Bifidobacterium animalis* subsp. *lactis* subsp. nov.", International Journal of Systematic and Evolutionary Microbiology (2004) 54, pp. 1137-1143.
Jeffrey H. Miller, "Experiment 33 Penicillin and Ampicillan Treatment for the Isolation of Auxotrophic Mutants", Experiments in Molecular Genetics, 1972, Cold Springs Harbor Laboratory, pp. 230-234.
Opinion of the Scientific Committee on Animal Nutrition on the Criteria for Assessing the Safety of Micro-Organisms Resistant to Antibiotics of Human Clinical and Veterinary Importance, European Commission Health & Consumer Protection Directorate-General, (2003) pp. 1-21.
Susana Delgado et al., "Antibiotic Susceptibility of *Lactobacillus* and *Bifidobacterium* Species from the Human Gastrointestinal Tract", Current Microbiology, vol. 50, (2005), pp. 202-207.
A.M. Yazid et al., "Antimicrobial susceptibility of bifidobacteria", Letters in Applied Microbiology 2000, 31, 57-62.
L. Masco et al., "Antimicrobial susceptibility of *Bifidobacterium* strains from humans, animals and probiotic products", Journal of Antimicrobial Chemotherapy (2006) 58, pp. 85-94.

(Continued)

Primary Examiner — Maria Leavitt
(74) Attorney, Agent, or Firm — Stephen A. Bent; Foley & Lardner LLP

(57) ABSTRACT

Many probiotic Bifidobacteriacea contains an active tetW that renders the cells resistant to tetracycline. This presents a theoretical risk of a horizontal transfer of functional antibiotic genes. The present invention relates to novel tetracycline-sensitive strains of the well-known probiotic *Bifidobacterium animalis* subsp. *lactis* strain BB-12® and the use of such novel strains for the preparation of a food or feed product or a dosage form comprising viable organisms.

3 Claims, No Drawings

OTHER PUBLICATIONS

J. Matto et al., "Comparison of three test media for antimicrobial susceptibility testing of bifidobacteria using the Etest method", International Journal of Antimicrobial Agents 28(2006) pp. 42-48.

C. Moubareck et al., "Antimicrobial susceptibility of bifidobacteria", Journal of Antimicrobial Chemotherapy (2005) 55, pp. 38-44.

Maria Saarela et al., "Tetracycline susceptibility of the ingested *Lactobacillus acidophilus* LaCH-5 and *Bifidobacterium animalis* subsp. *lactis* Bb-12 strains during antibiotic/probiotic intervention", International Journal of Antimicrobial Agents 29 (2007) pp. 271-280.

Shalini Mathur et al., "Antibiotic resistance in food lactic acid bacteria—a review", International Journal of Food Microbiology 105 (2005) pp. 281-295.

W.P. Charteris et al., "Antibiotic susceptibility of potentially probiotic *Bifidobacterium* isolates from the human gastrointestinal tract", Letters of Applied Microbiology 1998, 26, pp. 333-337.

William P. Charteris et al., "Gradient Diffusion Antibiotic Susceptibility Testing of Potentially Probiotic *Lactobacilli*", Journal of Food Protection, vol. 64, No. 12, 2001, pp. 2007-2014.

Atte von Wright, "Regulating the Safety of Probiotics—The European Approach", Current Pharmaceutical Design, 2005, 11, pp. 17-23.

Barry B. Bochner et al., "Positive Selection for Loss of Tetracycline Resistance", Journal of Bacteriology, vol. 143, No. 2, Aug. 1980, pp. 926-933.

K.S. Lim et al., "Antimicrobial Susceptibility of *Bifidobacteria*", J. Dairy Sci, 1993, 76:2168-2174.

SEQUENCE LISTING

<160> NUMBER OF SEQ ID NOS: 21

<210> SEQ ID NO 1
<211> LENGTH: 24
<212> TYPE: DNA
<213> ORGANISM: Bifidobacterium animalis subsp. lactis

<400> SEQUENCE: 1
ttgctgtcgg aaaaatacaa gctt          24

<210> SEQ ID NO 2
<211> LENGTH: 24
<212> TYPE: DNA
<213> ORGANISM: Bifidobacterium animalis subsp. lactis

<400> SEQUENCE: 2
ttgctgtcgg aaaatacaag cttg          24

-continued

```
<210> SEQ ID NO 3
<211> LENGTH: 12
<212> TYPE: DNA
<213> ORGANISM: Bifidobacterium animalis subsp. lactis

<400> SEQUENCE: 3
gaaaatacaa gc                                                              12

<210> SEQ ID NO 4
<211> LENGTH: 24
<212> TYPE: DNA
<213> ORGANISM: Bifidobacterium animalis subsp. lactis

<400> SEQUENCE: 4
tgctttgaat acgggcttta ttac                                                 24

<210> SEQ ID NO 5
<211> LENGTH: 24
<212> TYPE: DNA
<213> ORGANISM: Bifidobacterium animalis subsp. lactis

<400> SEQUENCE: 5
tgctttgaat acaggcttta ttac                                                 24

<210> SEQ ID NO 6
<211> LENGTH: 12
<212> TYPE: DNA
<213> ORGANISM: Bifidobacterium animalis subsp. lactis

<400> SEQUENCE: 6
gaatacaggc tt                                                              12

<210> SEQ ID NO 7
<211> LENGTH: 30
<212> TYPE: DNA
<213> ORGANISM: artificial
<220> FEATURE:
<223> OTHER INFORMATION: oligo

<400> SEQUENCE: 7
cggcacctgc tgtataatgc ggattgtggc                                           30

<210> SEQ ID NO 8
<211> LENGTH: 24
<212> TYPE: DNA
<213> ORGANISM: artificial
<220> FEATURE:
<223> OTHER INFORMATION: oligo

<400> SEQUENCE: 8
gcccttcggg gcagtaaagg gagg                                                 24

<210> SEQ ID NO 9
<211> LENGTH: 23
<212> TYPE: DNA
<213> ORGANISM: artificial
<220> FEATURE:
<223> OTHER INFORMATION: oligo

<400> SEQUENCE: 9
gcagacggtg tcgctgtccc cgg                                                  23

<210> SEQ ID NO 10
<211> LENGTH: 26
<212> TYPE: DNA
<213> ORGANISM: artificial
```

```
<220> FEATURE:
<223> OTHER INFORMATION: oligo

<400> SEQUENCE: 10
ggctggcgtt gatttgcaga gcgtgg                                          26

<210> SEQ ID NO 11
<211> LENGTH: 22
<212> TYPE: DNA
<213> ORGANISM: artificial
<220> FEATURE:
<223> OTHER INFORMATION: oligo

<400> SEQUENCE: 11
ggggagcgcc gccctatgcg gc                                              22

<210> SEQ ID NO 12
<211> LENGTH: 27
<212> TYPE: DNA
<213> ORGANISM: artificial
<220> FEATURE:
<223> OTHER INFORMATION: oligo

<400> SEQUENCE: 12
cgaggtgccg cccaacccgt tttgggc                                         27

<210> SEQ ID NO 13
<211> LENGTH: 26
<212> TYPE: DNA
<213> ORGANISM: artificial
<220> FEATURE:
<223> OTHER INFORMATION: oligo

<400> SEQUENCE: 13
ggagcggccg ctcaaagcag ccagcc                                          26

<210> SEQ ID NO 14
<211> LENGTH: 24
<212> TYPE: DNA
<213> ORGANISM: artificial
<220> FEATURE:
<223> OTHER INFORMATION: oligo

<400> SEQUENCE: 14
gcgaggaagg ttattgcatt tccc                                            24

<210> SEQ ID NO 15
<211> LENGTH: 30
<212> TYPE: DNA
<213> ORGANISM: artificial
<220> FEATURE:
<223> OTHER INFORMATION: oligo

<400> SEQUENCE: 15
gggagtgacc ccgccgatca tgcgaccatc                                      30

<210> SEQ ID NO 16
<211> LENGTH: 2220
<212> TYPE: DNA
<213> ORGANISM: Bifidobacterium animalis subsp. lactis

<400> SEQUENCE: 16
tcggcacctg ctgtataatg cggattgtgg catttgtgcg gtgttgcctt aaataaaact     60
ataatcaaat agtgggaaca aaggattatg atagtccctt ttgtagggc ttagtttttt      120 gtacccaatt taagaatact tttgccttat caatttttgac atatccccaa aaacagcact    180
```

```
cacaaacagg tgtatgctgt atatgtgtat gtccgcaaat tatcatcccc agtggtaaaa    240
gtattttact gctggggatt tttatgccct tcggggcagt aaagggagga caatcacatg    300
aaaataatca atattggaat tcttgcccat gtagacgctg gaaagacgac cttgacggag    360
agcctgctat atgccagcgg agccatttca gaaccgggga gcgtcgaaaa agggacaacg    420
aggacggaca ccatgctttt ggagcggcag cgtgggatta ccattcaagc ggcagtcact    480
tccttccagt ggcacagatg taaagtcaac attgtggata cgcccggcca catggatttt    540
ttggcggagg tgtaccgctc tttggctgtt ttagatgggg ccatcttggt gatctccgct    600
aaagatggcg tgcaggccca gacccgtatt ctgttccatg ccctgcggaa aatgaacatt    660
cccaccgtta tctttatcaa caagatcgac caggctggcg ttgatttgca gagcgtggtt    720
cagtctgttc gggataagct ctccgccgat attatcatca agcagacggt gtcgctgtcc    780
ccggaaatag tcctggagga aaataccgac atagaagcat gggatgcggt catcgaaaat    840
aacgataaat tattggaaaa gtatatcgca ggagaaccaa tcagccggga aaaacttgtg    900
cgggaggaac agcggcgggt tcaagacgcc tccctgttcc cggtctatta tggcagcgcc    960
aaaaagggcc ttggcattca accgttgatg gatgcggtga cagggctgtt ccaaccgatt   1020
ggggaacagg ggagcgccgc cctatgcggc agcgttttca aggtggagta tacagattgc   1080
ggccagcggc gtgtctatct acggctatac agcggaacgc tgcgcctgcg ggatacggtg   1140
gccctggccg ggagagaaaa gctgaaaatc acagagatgc gtattccatc caaggggaa    1200 attgttcgga cagacaccgc ttatccgggt gaaattgtta tccttcccag cgacagcgtg   1260
aggttaaacg atgtattagg ggacccaacc cggctccctc gtaaaaggtg gcgtgaggac   1320
cccctcccca tgctgcggac gtcgattgcg ccgaaaacgg cagcgcaaag agaacggctg   1380
ctggacgctc ttacgcaact gcggatact gacccgcttt tgcgctgcga ggtggattcc    1440
atcacccatg agatcattct ttcttttttg ggcggggtgc agttggaggt tgtttccgct   1500
ttgctgtcgg aaaaatacaa gcttgaaaca gtggtaaagg aacccaccgt catttatatg   1560
gagcggccgc tcaaagcagc cagccacacc atccatatcg aggtgccgcc caacccgttt   1620
tgggcatcca tcggactgtc tgttacacca ctcccgcttg gctccggtgt acaatacaag   1680
agccgggttt cgctgggata cttgaaccag agttttcaaa acgctgtcag ggatggtatc   1740
cgttacgggc tggagcaggg cttgttcggc tggaacgtaa cggactgtaa gatttgcttt   1800
gaatacgggc tttattacag tccggtcagc acgccggcgg acttccgctc attggccccg   1860
attgtattgg aacaggcatt gaaggaatca gggacgcaac tgctggaacc ttatctctcc   1920 ttcacctct atgcgccccg ggaatatctt tccagggctt atcatgatgc accgaaatac    1980
tgtgccacca tcgaaacggt ccaggtaaaa aaggatgaag ttgtctttac tggcgagatt   2040
cccgcccgct gtatacaggc ataccgtact gatctggcct tttacaccaa cgggcagagc   2100
gtatgcctta cagaactgaa agggtatcag gccgctgtcg gcaagccagt catccagccc   2160
cgccgtccaa acagccgcct ggacaaggtg cgccatatgt tcagtaagat cacttgatac   2220
```

<210> SEQ ID NO 17
<211> LENGTH: 30
<212> TYPE: DNA
<213> ORGANISM: Bifidobacterium animalis subsp. lactis

<400> SEQUENCE: 17

```
gaaaaataca agcttgaaac agtggtaaag                                       30
```

```
<210> SEQ ID NO 18
<211> LENGTH: 10
<212> TYPE: PRT
<213> ORGANISM: Bifidobacterium animalis subsp. lactis

<400> SEQUENCE: 18

Glu Lys Tyr Lys Leu Glu Thr Val Val Lys
1               5                   10

<210> SEQ ID NO 19
<211> LENGTH: 27
<212> TYPE: DNA
<213> ORGANISM: Bifidobacterium animalis subsp. lactis

<400> SEQUENCE: 19
gaaaatacaa gcttgaaaca gtggtaa                                        27

<210> SEQ ID NO 20
<211> LENGTH: 8
<212> TYPE: PRT
<213> ORGANISM: Bifidobacterium animalis subsp. lactis

<400> SEQUENCE: 20

Glu Asn Thr Ser Leu Lys Gln Trp
1               5

<210> SEQ ID NO 21
<211> LENGTH: 635
<212> TYPE: PRT
<213> ORGANISM: Bifidobacterium animalis subsp. lactis

<400> SEQUENCE: 21

Met Lys Ile Ile Asn Ile Gly Ile Leu Ala His Val Asp Ala Gly Lys
1               5                   10                  15

Thr Thr Leu Thr Glu Ser Leu Leu Tyr Ala Ser Gly Ala Ile Ser Glu
                20                  25                  30

Pro Gly Ser Val Glu Lys Gly Thr Thr Met Leu Leu Glu Arg Gln Arg
            35                  40                  45

Gly Ile Thr Ile Gln Ala Ala Val Thr Ser Phe Gln Trp His Arg Cys
        50                  55                  60

Lys Val Asn Ile Val Asp Thr Pro Gly His Met Asp Phe Leu Ala Glu
65                  70                  75                  80

Val Tyr Arg Ser Leu Ala Val Leu Asp Gly Ala Ile Leu Val Ile Ser
                85                  90                  95

Ala Lys Asp Gly Val Gln Ala Gln Thr Arg Ile Leu Phe His Ala Leu
            100                 105                 110

Arg Lys Met Asn Ile Pro Thr Val Ile Phe Ile Asn Lys Ile Asp Gln
        115                 120                 125

Ala Gly Val Asp Leu Gln Ser Val Val Gln Ser Val Arg Asp Lys Leu
    130                 135                 140

Ser Ala Asp Ile Ile Ile Lys Gln Thr Val Ser Leu Ser Pro Glu Ile
145                 150                 155                 160

Val Leu Glu Glu Asn Thr Asp Ile Glu Ala Trp Asp Ala Val Ile Glu
                165                 170                 175

Asn Asn Asp Lys Leu Leu Glu Lys Tyr Ile Ala Gly Glu Pro Ile Ser
            180                 185                 190

Arg Glu Lys Leu Val Arg Glu Glu Gln Arg Val Gln Asp Ala Ser
        195                 200                 205

Leu Phe Pro Val Tyr Tyr Gly Ser Ala Lys Lys Gly Leu Gly Ile Gln
    210                 215                 220
```

```
Pro Leu Met Asp Ala Val Thr Gly Leu Phe Gln Pro Ile Gly Glu Gln
225                 230                 235                 240

Gly Ser Ala Ala Leu Cys Gly Ser Val Phe Lys Val Glu Tyr Thr Asp
            245                 250                 255

Cys Gly Gln Arg Arg Val Tyr Leu Arg Leu Tyr Ser Gly Thr Leu Arg
        260                 265                 270

Leu Arg Asp Thr Val Ala Leu Ala Gly Arg Glu Lys Leu Lys Ile Thr
    275                 280                 285

Glu Met Arg Ile Pro Ser Lys Gly Glu Ile Val Arg Thr Asp Thr Ala
290                 295                 300

Tyr Pro Gly Glu Ile Val Ile Leu Pro Ser Asp Ser Val Arg Leu Asn
305                 310                 315                 320

Asp Val Leu Gly Asp Pro Thr Arg Leu Pro Arg Lys Arg Trp Arg Glu
            325                 330                 335

Asp Pro Leu Pro Met Leu Arg Thr Ser Ile Ala Pro Lys Thr Ala Ala
        340                 345                 350

Gln Arg Glu Arg Leu Leu Asp Ala Leu Thr Gln Leu Ala Asp Thr Asp
    355                 360                 365

Pro Leu Leu Arg Cys Glu Val Asp Ser Ile Thr His Glu Ile Ile Leu
370                 375                 380

Ser Phe Leu Gly Arg Val Gln Leu Glu Val Val Ser Ala Leu Leu Ser
385                 390                 395                 400

Glu Lys Tyr Lys Leu Glu Thr Val Val Lys Glu Pro Thr Val Ile Tyr
            405                 410                 415

Met Glu Arg Pro Leu Lys Ala Ala Ser His Thr Ile His Ile Glu Val
        420                 425                 430

Pro Pro Asn Pro Phe Trp Ala Ser Ile Gly Leu Ser Val Thr Pro Leu
    435                 440                 445

Pro Leu Gly Ser Gly Val Gln Tyr Lys Ser Arg Val Ser Leu Gly Tyr
450                 455                 460

Leu Asn Gln Ser Phe Gln Asn Ala Val Arg Asp Gly Ile Arg Tyr Gly
465                 470                 475                 480

Leu Glu Gln Gly Leu Phe Gly Trp Asn Val Thr Asp Cys Lys Ile Cys
            485                 490                 495

Phe Glu Tyr Gly Leu Tyr Tyr Ser Pro Val Ser Thr Pro Ala Asp Phe
        500                 505                 510

Arg Ser Leu Ala Pro Ile Val Leu Glu Gln Ala Leu Lys Glu Ser Gly
    515                 520                 525

Thr Gln Leu Leu Glu Pro Tyr Leu Ser Phe Thr Leu Tyr Ala Pro Arg
530                 535                 540

Glu Tyr Leu Ser Arg Ala Tyr His Asp Ala Pro Lys Tyr Cys Ala Thr
545                 550                 555                 560

Ile Glu Thr Val Gln Val Lys Lys Asp Glu Val Val Phe Thr Gly Glu
            565                 570                 575

Ile Pro Ala Arg Cys Ile Gln Ala Tyr Arg Thr Asp Leu Ala Phe Tyr
        580                 585                 590

Thr Asn Gly Gln Ser Val Cys Leu Thr Glu Leu Lys Gly Tyr Gln Ala
    595                 600                 605

Ala Val Gly Lys Pro Val Ile Gln Pro Arg Arg Pro Asn Ser Arg Leu
610                 615                 620

Asp Lys Val Arg His Met Phe Ser Lys Ile Thr
625                 630                 635
```

TETRACYCLINE-SENSITIVE BIFIDOBACTERIA STRAINS

FIELD OF THE INVENTION

The present invention pertains to novel tetracycline-sensitive strains obtained from tetracycline-resistant probiotic strains of the genus of *Bifidobacterium* carrying an inactivated tetW on its chromosome, and the use of such novel strains for the preparation of a food or feed product or a dosage form comprising viable organisms.

BACKGROUND OF THE INVENTION

Bacteria, which ferment sugars with the production of acids, in particular lactic acid as a major metabolic component have been known for a long time. Such bacteria may be found in milk or milk products, living or decaying plants but also in the intestine of man and animals. Traditionally, these bacteria have been referred to as "lactic acid bacteria". Lactic acid bacteria designates a rather heterogeneous group of Gram positive, non-motile, microaerophilic or anaerobic bacteria which ferment sugar with the production of acids including lactic acid and comprise e.g. the genera *Bifidobacterium, Enterococcus, Lactobacillus, Lactococcus, Leuconostoc* and *Pediococcus*.

For centuries lactic acid bacteria have been used in the manufacture of food and feed products including most dairy products. Today lactic acid bacteria are essential in the making of all fermented milk products such as yoghurt, cheese and butter. Furthermore, lactic acid bacteria are widely used in the meat processing industry, wine-manufacturing industry, and the juice manufacturing industry as well as a number of other industries.

Cultures of lactic acid bacteria also find important uses in the biopreservation of food-stuffs.

The publication of a large amount of reports documenting that various lactic bacteria beneficially affect the well-being of humans and/or animals have attracted even further interest to this group of bacteria. In particular, specific strains of *Lactobacillus* or *Bifidobacterium* have been found to be able to colonize the intestinal mucosa and to assist in the maintenance of the well being of the hosts.

EP 0 768 375 describes specific strains of *Bifidobacterium* ssp, that are capable to become implanted in the intestinal flora and being capable to competitively exclude adhesion of pathogenic bacteria to intestinal cells. These *Bifidobacteria* are reported to assist in immunomodulation and thus in the maintenance of the individual's health. The immunomodulation effect of *Bifidobacteria* may even be conferred onto unborn children. WO 01/97822 e.g. describes that intake of *Bifidobacterium animalis* strain BB-12® by the mother during her pregnancy reduces the occurrence of atrophic diseases in children. Also WO 03/099037 describe that *Bifidobacterium animalis* strain BB-12® are able to beneficially modify the immune response. According to Masco et al. (2004) *Bifidobacterium animalis* strain BB-12® should correctly be referred to as *Bifidobacterium animalis* subsp. *lactis* strain BB-12®. In the present context *Bifidobacterium animalis* strain 66-12® and *Bifidobacterium animalis* subsp. *lactis* strain BB-12® are used synonymously.

Probiotic microorganisms have been defined as "Live microorganisms which when administered in adequate amounts confer a health benefit on the host" (FAO/WHO 2002). During the recent years, documentation on probiotic properties of *Bifidobacteria* and other lactic bacteria has accumulated. In general the probiotic activity is associated with specific strains. The previously mentioned *Bifidobacterium animalis* subsp. *lactis* strain BB-12® as well as *Bifidobacterium lactis* strain HN019 have been reported as probiotic (WO 01/97822, WO 03/099037, Zhou et al. (2005), U.S. Pat. No. 6,379,663).

Worldwide there is widespread public concern that the number of antibiotic resistant pathogenic bacteria increases dramatically. All available data indicate that the disturbing increase in antibiotic resistant pathogenic bacteria is caused by an extensive and very liberal use of antibiotics in the general population as well as in animal husbandry.

It is a well-established fact that many antibiotic resistant bacteria carry genetic determinants, genes, which confer resistance to one or more antibiotics. It is furthermore well known that such genetic determinants under certain circumstances are transferable and may confer the antibiotic-resistant phenotype to recipient bacteria.

For these reasons, it may be of concern to ingest even beneficially, non-pathogenic bacteria if they do contain an antibiotic resistant determinant. This concern is further emphasized in the report from the European Commission (SCAN 2003) stating that the presence of a known resistance gene is not acceptable (page 21).

Resistance to tetracycline is the most common bacterial antibiotic resistance found in nature and similarly it is the most widely distributed type of resistance among bacteria isolated from animals (Billington 2002). Tetracycline inhibits protein synthesis by binding to a single high-affinity site on the 30S ribosomal subunit. With tetracycline in this position, the binding of aminoacyl-tRNA to the A site is prevented and thus protein synthesis is blocked.

Resistance to tetracycline may be mediated either by active efflux of tetracycline from the cell, by ribosomal protection by one or more soluble protein(s), the so-called ribosomal protection proteins (RPPs), or by enzymatic inactivation of tetracycline.

Recently, a new ribosome-protection-type tetracycline resistance (Tet$^r$) gene, tetW, was identified in rumen isolates of *Butyrivibrio fibrisolvens* and a number of other rumen bacteria (Barbosa, 1999).

Although the tetW determinant is widely distributed among tetracycline resistant isolates of animal pathogens (Billington 2002) it was a surprise for the authors of this application to find that all known probiotic strains of *Bifidobacterium animalis* subsp. *lactis*, including the two well-known *Bifidobacterium* strains BB-12® and DR10™, carry a functional tetW determinant and are resistant to tetracycline; in particular because the DR10™ strain as well as the BB-12® strain were reported to be tetracycline sensitive in a recent report (Zhou et al. 2005).

As the commercial interests in probiotic Bifidobacteriacea are strongly related to their contemplated health beneficial effects it is clear that any properties that may infer a risk of health detrimental effects such, as the presence of a functional antibiotic-resistance gene, is highly unwanted. Consequently, it appear highly advantageous to be able to provide new variations of probiotic *Bifidobacterium* strains wherein the tetW resistance gene is inactivated as such new strains drastically reduce the risk of transfer of the antibiotic resistance trait to other bacteria.

SUMMARY OF THE INVENTION

The problem to be solved by the present invention is to provide new variations of the tetracycline resistant probiotic

*Bifidobacterium animalis* subsp. *lactis* strain BB-12® which reduce the risk of a horizontal transfer of functional antibiotic resistant genes.

The solution, according to the first aspect of the invention, is the provision of a *Bifidobacterium animalis* subsp. *lactis* strain containing an inactivated tetW on its chromosome obtainable by the process comprising the steps of:

a. subjecting a culture of *Bifidobacterium animalis* subsp. *lactis* strain BB-12® cells, comprising a functional tetW on its chromosome and having a Minimum Inhibitive Concentration (MIC) of 4 microgram tetracycline/ml or higher, to a chemical mutagen which is ethidium bromide (EtBr), b. subjecting the cells to a physical mutagen which is ultra violet light (UV), c. transfer an aliquot of the UV treated culture to fresh medium containing a dose of tetracycline which is inhibitory to the growth of cells with an inactivated tetW, but tolerable to cells with a functional tetW, d. add a dose of penicillin or an analogue of penicillin (eg. ampicillin) which is detrimental to exponentially growing cells, but tolerable to non-growing cells, and continue to culture the cells, e. isolate cells that have acquired antibiotic sensitivity defined as having a MIC of 1.5 microgram tetracycline/ml or less, f. analyse the chromosomal tetW of said isolated, antibiotic sensitive cells, and g. select and expand antibiotic sensitive cells which is mutated in tetW, wherein the mutated cell with an inactivated tetW is selected from the group consisting of the *Bifidobacterium animalis* subsp. *lactis* strains with the registration number DSM 18735 (CHCC 9870) or DSM 18776 (CHCC 9884) and a mutant strain, said mutant strain is obtained by using any of the deposited strains CHCC 9870 or CHCC 9884 as starting material and said mutant strain have a MIC of 1.5 microgram tetracycline/ml or less.

As can be seen in the working examples such strains stably maintain the tetW inactivated genotype and accordingly present a significant reduction of the risk of horizontal transfer of functional tetW resistant gene.

A second aspect of the invention relates to starter culture composition comprising any of of the *Bifidobacterium animalis* subsp. *lactis* strains selected from the group of strains with the registration number DSM 18735 (CHCC 9870), DSM 18776 (CHCC 9884) and a mutant strain thereof, wherein the mutant strain is obtained by using any of the deposited strains as starting material and have a MIC of 1.5 microgram tetracycline/ml or less.

Further aspects of the invention are the use of any of the previous mentioned *Bifidobacterium animalis* subsp. *lactis* strains containing an inactivated tetW on its chromosome for the preparation of an ingestible material or a bacterial culture, including a method of manufacturing a food or feed product comprising adding a starter culture composition comprising any of the *Bifidobacterium animalis* subsp. *lactis* strains containing an inactivated tetW gene to a food or feed product starting material and keeping the thus inoculated starting material under conditions where the lactic acid bacterium is metabolically active Also the use of any of said *Bifidobacterium animalis* subsp. *lactis* strains with an inactivated tetW gene for the manufacture of a medicament as well as a food or feed product comprising any of these *Bifidobacterium animalis* subsp. *lactis* strains are aspects of the present invention

DETAILED DISCLOSURE OF THE INVENTION

Novel *Bifidobacterium animalis* subsp. *lactis* Strains

A sample of the novel *Bifidobacterium animalis* subsp. *lactis* strain CHCC9870 (Bb12tetW-570) has been deposited at DSMZ (Deutsche Sammlung von Mikroorganismen und Zellkulturen GmbH) under the accession number DSM 18735 with a deposit date of 26 Oct. 2006. The deposit has been made under the conditions of the Budapest Treaty on the International Recognition of the Deposit of Microorganisms for the Purposes of Patent Procedure.

Likewise a sample of the novel *Bifidobacterium animalis* subsp. *lactis* strain CHCC9884 (Bb12tetW-S705) has been deposited at DSMZ (Deutsche Sammlung von Mikroorganismen und Zellkulturen GmbH) under the accession number DSM 18776 with a deposit date of 9 Nov. 2006. Also this deposit has been made under the conditions of the Budapest Treaty on the International Recognition of the Deposit of Microorganisms for the Purposes of Patent Procedure.

As described in example 1 the novel *Bifidobacterium animalis* subsp. *lactis* strain Bb12tetW-S70 (CHCC9870; DSM 18735) as well as the novel *Bifidobacterium animalis* subsp. *lactis* strain Bb12tetW-S705 (CHCC9884; DSM 18776) were both obtained by a process comprising subjecting a culture of *Bifidobacterium animalis* subsp. *lactis* strain BB-12® to a dual mutagenic approach. BB-12® is a well-established, probiotic strain it has the accession number CHCC5445 in the Hansen culture collection and was deposited on Sep. 30, 2003 according to the Budapest Treaty on the International Recognition of the Deposit of Microorganisms for the Purposes of Patent Procedure with the Deutsche Sammlung von Mikroorganismen and Zellkulturen under accession number DSM15954.

BB-12® comprise a functional tetW on its chromosome and have a Minimal Inhibitive Concentration (MIC) which is higher that 4 microgram tetracycline/ml as determined by the to Etest susceptibility method described by M. Danielsen and A. Wind (2003)

The Etest susceptibility method was performed essentially as described by M. Danielsen and A. Wind (2003). Briefly, the test comprise the steps of:

a) dipping a sterile cotton swab into a culture of a tetracycline sensitive strain to be tested, which has grown overnight, b) streaking the entire surface of a MRS agar plate (diameter: 8.5 cm) evenly in three directions with the cotton swab of step a), (MRS is a general medium to grow Lactobacilli and other lactic acid bacteria, the MRS agar plate is made as described by the manufacturer of the MRS-Broth (Difco 288110), Difco laboratories, Detroit, Mich.)

c) when the inoculum applied in step b) has dried, a so-called E-test strip (AB BIODISK, Sweden) is applied onto the agar surface with the MIC scale facing upwards by use of a manual applicator.

d) the agar plates are then incubated under anaerobic or microaerophilic conditions in an inverted position at 37° C. overnight.

e) finally the MIC value is determined by reading the value where the edge of the inhibition ellipse intersects the strip.

The method and the E-test strip are further described in EP157071 which is incorporated herein by reference.

As further discussed in example 1 the BB-12® cells were subjected to the chemical mutagen ethidium bromide (EtBr)

and then subjected to ultra violet light (UV). Following the mutagenization, the cells were subjected to an ampicillin enrichment procedure. This imply transferring an aliquot of the UV treated culture to fresh medium containing a dose of penicillin or an analogue of penicillin which is detrimental to exponentially growing cells, but tolerable to non-growing cells, and culture the cells in said penicillin analogue comprising medium under conditions which promote growth of non-mutated cells in the absence penicillin or an analogue of penicillin such as ampicillin. As described in example 2 the ampicillin enrichment procedure was used to enrich for tetracycline sensitive mutants by transferring the cells to a medium containing a dose of tetracycline (e.g. 10 microgram/ml), which arrest the growth of tetracycline-sensitive cells, incubate the cells under growth conditions, and add a penicillin analogue and continue the incubation.

The cells of the ampicillin-enriched culture were then harvested, and tetracycline sensitive mutants with a MIC of 1.5 microgram tetracycline/ml or less are isolated by standard replica plating techniques.

As illustrated in example 2 the obtained mutants demonstrated a MIC value less than 1 microgram tetracycline/ml in casu 0.5 microgram tetracycline/ml. The mutants was expanded and analyzed with respect to the DNA-sequence of their tetW (example 3). This analysis showed that the mutant strain named Bb12Tet-S70 (CHCC9870; DSM 18735) comprise a frame-shift mutation at nucleotide position #1515 of SEQ ID NO.:16 caused by the deletion of the adenine in position #1515 of SEQ ID NO.:16.

This frame-shift introduces a stop codon 7 codons downstream from the frame-shift and results in the inactivation of tetW as indicated by the observed MIC of 0.5 microgram tetracycline/ml.

The DNA-sequence analysis of the mutant named Bb12Tet-S705 (CHCC9884; DSM 18776) demonstrated that this mutant comprise a transition of guanine to adenine at nucleotide position #1807 of SEQ ID NO.:16. The transition result in a mis-sense mutation: glycine to arginine, and result in the inactivation of tetW as indicated by the observed MIC of 0.5 microgram tetracycline/ml.

By the expression "tetracycline-resistant" is referred to a bacterium which have a minimum inhibitive concentration (MIC) of tetracycline of at least higher than 4 microgram/ml (EFSA, 2005), for instance at least 5 microgram/ml, such as at least 8 microgram/ml including at least 10 microgram/ml or even at least 15 microgram tetracycline/ml. The MIC value may in particular be determined by the "Etest" susceptibility screening method as described by Danielsen and Wind (2003). The minimum inhibitive concentration is the lowest concentration that results in inhibition of visible growth.

In the present context the expression "sensitive to tetracycline" refer to a bacterium which have a MIC of 1.5 microgram tetracycline/ml or less, such as 1 microgram/ml or even less than 0.75 microgram tetracycline/ml, as determined by the "Etest" susceptibility screening method.

As illustrated in example 4 the Bb12Tet-S70 (CHCC9870; DSM 18735) strain revert from a tetracycline-sensitive to a tetracycline-resistant phenotype with a rate of approximately $0.8 \times 10^{-9}$ and the Bb12Tet-S705 (CHCC9884; DSM 18776) strain have a rate of approximately $6 \times 10^{-9}$. Although Bb12Tet-S705 is more prone to reversion than Bb12Tet-S70, both strains are sufficiently stable to fulfill the objective of providing new variations of the probiotic BB-12® with a reduced risk of transfer of tetracycline to other bacteria. However, due to its higher genetic stability the most preferred embodiment of the present preferred embodiment of the present invention is the bacterial strain which is identified as Bifidobacterium animalis subsp. *lactis* subspecies *lactis* strain Bb12Tet-S70 (CHCC9870; DSM 18735).

As used herein the term "mutant" is comprised by the conventional meaning of that term i.e. it refers to bacterial strains that are genetically different from their progenitor cells. Mutations can be obtained by subjecting a microbial strain to any conventionally used mutagenization treatment including treatment with a chemical mutagen such as EtBr, ethanemethane sulphonate (EMS) or N-methyl-N'-nitro-N-nitroguanidine (NTG), UV light or to spontaneously occurring mutants which are selected on the basis of desired characteristics such as e.g. resistance to antibiotics, bile- and/or gastric acid. It is envisaged that useful mutants also can be provided by recombinant DNA technology including site-directed mutagenesis, PCR techniques and other in vitro or in vivo modifications.

It is clear for the skilled person that by using the two strains (Bb12Tet-S70(CHCC9870) and Bb12Tet-S705 (CHCC9884) as starting material (progenitor cells) the skilled person can by conventional mutagenesis and/or re-isolation techniques routinely obtain further mutants or derivatives thereof that retain the herein described relevant features and advantages. Accordingly, such mutant strains are an aspect of the present invention. Useful mutants of the two strains may also be obtained by use of recombinant DNA technology, such mutants are also an embodiment of the present invention.

Preferred strains are those having a MIC that is 1.5 microgram tetracycline/ml or less, such as 1 microgram/ml or even less than 0.75 microgram tetracycline/ml as determined by the "Etest" susceptibility screening method.

Such strains, which harbor a mutated tetW, are particularly preferred embodiments of the invention.

The inactivating mutation of the tetW gene that renders the new strains sensitive to tetracyclines may typically be described in relation to the tetW gene sequence of the relevant progenitor cell.

As described in the examples suitable tetracycline-sensitive strains with an inactivated tetW can be achieved by introducing specific mutations in the tetW gene.

In one preferred embodiment of the invention an "ochre" stop codon has been introduced in the tetW by changing part of chromosomally encoded tetW that is characterized by the sequence TTG CTG TCG GAA AAA TAC AAG CTT [SEQ ID NO.:1] to TTG CTG TCG GAA̅ MT ACA AGC TTG [SEQ ID NO.:2], the deleted base in the functional tetW is indicated by underscoring. Thus a *Bifidobacterium animalis* subsp. *lactis* which comprise the sequence: GAA AAT ACA AGC [SEQ ID NO.:3] in its tetW gene and which is derived from Bb12Tet-S70 (CHCC9870; DSM 18735) or Bb12Tet-S705 (CHCC9884; DSM 18776) is a preferred embodiment of the present invention.

We also observed that the tetW gene could be inactivated, and result in sensitivity to tetracycline, by changing the part of chromosomally encoded tetW which comprise the sequence: TGC TTT GAA TAC GGG CTT TAT TAC [SEQ ID NO.:4] to TGC TTT GAA TAC̅ AGG CTT TAT TAC [SEQ ID NO.:5] this mutation introduce an "missense" codon in tetW and the mutated base in the functional tetW is underscored. Such a *Bifidobacterium animalis* subsp. *lactis* which comprise the sequence: GAA TAC AGG CTT [SEQ ID NO.:6] in its tetW gene and which is derived from Bb12Tet-S70 (CHCC9870; DSM 18735) or Bb12Tet-S705 (CHCC9884; DSM 18776) is another preferred embodiment of the present invention. Also a bacterial strain wherein the tetW gene comprise at least one sequence selected from the group of SEQ ID NO.:NO:3

[GAA AAT ACA AGC] and SEQ ID NO.:6 [GAA TAC AGG CTT] is also an embodiment of the present invention.

Bifidobacteria and other lactic acid bacteria are commonly used as starter cultures serving a technological purpose in the production of various foods. The most well known industry using starter cultures is the dairy industry, but starter cultures are also used widely in the production of non-dairy food and feed products. A starter culture that comprise at least one of the strains of the invention is an embodiment of the invention.

Typically, such a starter culture composition comprises the bacteria in a concentrated form including frozen, dried or freeze-dried concentrates typically having a concentration of viable cells, which is in the range of $10^4$ to $10^{12}$ cfu (colony forming units) per gram of the composition including at least $10^4$ cfu per gram of the composition, such as at least $10^5$ cfu/g, e.g. at least $10^6$ cfu/g, such as at least $10^7$ cfu/g, e.g. at least $10^8$ cfu/g, such as at least $10^9$ cfu/g, e.g. at least $10^{10}$ cfu/g, such as at least $10^{11}$ cfu/g.

The composition may as further components contain cryoprotectants and/or conventional additives including nutrients such as yeast extracts, sugars and vitamins. A particularly preferred group of cryoprotectants is selected from the group consisting of inosine-5'-monophosphate (IMP), adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any of such compounds.

As it is normal in the production of lactic acid bacterial fermentation processes to apply mixed cultures of lactic acid bacteria, the starter composition will in certain embodiments comprise a multiplicity of strains either belonging to the same species or belonging to different species. A typical example of such a useful combination of lactic acid bacteria in a starter culture composition is a mixture of a *Bifidobacterium animalis* subsp. *lactis* strain of the invention and one or more *Lactococcus* spp., *Streptococcus* spp., *Lactobacillus* spp., *Leuconostoc* spp., *Pediococcus* spp., *Brevibacterium* spp. and *Propionibacterium* spp. strain(s) in addition to at least one of the strains of the present invention.

Another aspect of the invention relates to a method of manufacturing a food or feed product comprising adding a starter culture composition as described herein to a food or feed product starting material and keeping the thus inoculated starting material under conditions where the lactic acid bacterium is metabolically active.

Useful food product starting materials include any material which is conventionally subjected to a lactic acid bacterial fermentation step such as milk, vegetable materials, meat products, fruit juices, must, doughs and batters.

The fermented products, which are obtained by the method, include as typical examples dairy products such as fermented milk, yoghurt, cheese including fresh cheese products or mozzarella, and buttermilk.

Although *Bifidobacteria* and other lactic acid bacteria are commonly used as starter cultures serving a technological purpose in the production of various foods, *Bifidobacteria* can also serve as probiotics i.e. as live non-pathogenic organisms, which have health benefits when taken orally in foods, capsules, tablets or other dosage forms.

Consequently it is an important aspect of the present invention to use the *Bifidobacteria* strains of the invention for the preparation of an ingestible material or a bacterial culture.

It will be understood that the organism to be comprised in the composition according to the invention can be provided in the form of a liquid, in a frozen or dried form, such as e.g. freeze-dried, fluidized bed-dried or spray-dried.

Since *Bifidobacteria* in general are considered as probiotic organisms (Yazid, 2000) the use of a *Bifidobacteria* of the present invention as a probiotic is a preferred embodiment. The probiotic composition of the present invention can be any ingestible material selected from the group consisting of milk, curd, milk based fermented products, acidified milk, yoghurt, frozen yoghurt, milk powder, milk based powders, milk concentrate, cheese, cheese spreads, dressings beverages, ice-creams, fermented cereal based products, infant formulae, tablets, liquid bacterial suspensions, dried oral supplement, wet oral supplement, dry tube feeding or wet tubefeeding that is produced by use of the *Bifidobacteria* of this invention.

It may be desirable to administer the organism in the form of many oral dosage forms such as solid forms including capsules, tablets, granules, bulk powders or in a dried form, such as a freeze-dried or spay-dried form. A review of conventional formulation techniques can be found in e.g. "The Theory and Practice of Industrial Pharmacy" (Ed. Lachman L. et al, 1986) or Laulund (1994). Thus, the tablets may be prepared by methods known in the art and can be compressed, enterically coated, sugar coated, film coated or multiply compressed, containing suitable binders, lubricants, diluents, disintegrating agents, colouring agents, flouring agents, flow-inducing agents and melting agents.

Capsules, both soft and hard capsules, having liquid or solid contents, may be prepared according to conventional techniques which are well known in the pharmaceutical industry. As one example, the organisms may be filled into gelatine capsules, using a suitable filling machine.

It may also be convenient to provide the preparations in liquid oral dosages such as e.g. aqueous solutions, emulsions, suspensions, solutions and/or suspensions reconstituted from non-effervescent granules and effervescent preparations reconstituted from effervescent granules containing suitable solvents, preservatives, emulsifying agents, suspending agents, diluents, sweeteners, melting agents, colouring agents and flavouring agents. The liquid oral dosage form can also be in a form of a fermented dairy product such as yoghurt or sweet acidophilus milk or the above-mentioned fruit juice, comprising viable cells of the organism. It is also comprised by the invention to provide the organisms in an acid protected powder included in a food of low water activity or in a fat or wax phase of a food such as e.g. a functional food or feed.

In one embodiment, the ingestible material is a fermented food or feed product prepared by use of the *Bifidobacteria* of the present invention. The fermented food or feed product may be further processed. In a number of situations it has been reported that bacteria produces health promoting compounds during fermentation. In such cases it might be advantageous to fractionate and/or upconcentrate fractions of the fermented food product. One can even imagine that it in certain situations would be valuable to further process the fermented food product by pasteurization even though the beneficial *Bifidobacteria* are inactivated by such procedure. This is also an embodiment of the present invention.

However in general it is considered beneficial that the ingestible material should comprise live *Bifidobacteria* in an amount from about $10^5$ cfu/g to about $10^{12}$ cfu/g ingestible material, since living cells are a prerequisite for obtaining the probiotic effect.

A further important embodiment of the present invention is the use of the *Bifidobacteria* of the present invention to prepare a composition for the treatment, prevention of a disease, syndrome or condition, or for improving digestion of nutrients, or for improving the general health status of a human being or a vertebrate animal.

In a further embodiment, the composition further comprises a pharmaceutically acceptable carrier. As used herein, the term "pharmaceutically acceptable carrier" means one or more solid or liquid filler diluents or encapsulating substances which are suitable for administration to a human or an animal and which is/are compatible with the probiotically active organisms. The term "compatible" relates to components of the pharmaceutical composition which are capable of being commingled with the probiotic in a manner enabling no interaction because it would substantially reduce the probiotic efficacy of the organisms selected for the invention under ordinary use conditions. Pharmaceutically acceptable carriers must be of a sufficiently high purity and a sufficiently low toxicity to render them suitable for administration to humans and animals being treated.

In useful embodiments, the ingestible material according to the invention is suitable for preventing or treating a disease, syndrome or condition is selected from the group consisting of antibiotic-associated disorders, gastroenteritis, diarrhoea including traveller's diarrhoea and acute infantile diarrhoea, lactose intolerance, gastrointestinal infections and colonization of the gastrointestinal tract by pathogenic bacteria including *Helicobacter pylori* and *Clostridium difficile*, irritable bowel syndrome (IBS), inflammatory bowel disease (IBD) and other immunomodulative syndromes, colonic cancer, urogenital infections and tumours, vaginal infections, allergy (especially atopic eczema), vaccination, cholesterolemia and hypertension.

In further useful embodiments, the ingestible material according to the invention is suitable for preventing or treating infections with pathogens such as e.g. *Heliobacter pylori, Campylobacter pyloridis, Staphylococcus aureus, Staphylococcus epidermidis, Streptococcus pyogenes, Streptococcus pneumoniae, Enterococcus faecalis, Hemophilus influenzae, Escherichia coli, Klebsiella pneumoniae, Enterobacter cloacae, Citrobacter freundii, Serratia marcescens, Pseudomonas aeruginosa* and *Pseudomonas maltophilia, Salmonella* sp. and fungi such as *Candida albicans* and *Aspergillus fumigatus*, and combinations of these species.

In recent years rotaviruses and other enteric viruses have been identified as a major cause of infectious diarrhoea. Interestingly, *Bifidobacterium animalis* subsp. *lactis* BB-12® has been shown effectively to prevent or treat infections also with these pathogens. Thus in useful embodiments, the ingestible material according to the invention is used for preventing or treating infections with rotaviruses and other enteric viruses.

It may be useful to combine two or more of the above assumingly probiotically active organisms, such as e.g. a preparation comprising a *Lactobacillus* species and a *Bifidobacterium* species.

Performance of the Mutant Strains and their Benefits to Man.

The *Bifidobacterium animalis* subsp. *lactis* BB-12® (CHCC5445), is an extremely important strain for the health and well being of mammals due to its probiotic capabilities (e.g. immune stabilizing effect in humans, controlling of a balanced microflora in the digestive tract thereby reducing or acting as inhibitors of various epidemiologic syndromes, etc.). Although BB-12® strain harbors an active gene encoding resistance to tetracycline, the most prominent bacterial antibiotic resistance found in nature (Chopra and Roberts, 2001), it has for many years been used in food production, and to our knowledge without causing any harm. On the contrary only positive effect have been ascribed to the use of this strain. However, the fact that the strain contain an active tetW in its genome does possess the theoretical possibility of transferring the tetracycline resistance to other—and harmful—bacteria in the human digestive system. The risk of this increase if ingested donor bacteria survive in the gut in large numbers, as is the case with the typical use of probiotic bacteria. Inactivation of the tetW gene in the two variants, as it has been demonstrated here reduces the risk of a horizontal transfer of functional antibiotic resistant genes significantly.

Apart from the lesion in the tetW, the two tetracycline sensitive strains are probably isogenic with their progenitor strain BB-12® as suggested under Example 5. Consequently, it can be assumed that the two tetracycline sensitive strains possess most if not all the features that make BB-12® probiotic. Accordingly, the use of the strains of the present inventions as a probiotic is an important embodiment of the invention.

The Invention Presented in the Form of Claims

Preferred aspects and embodiments of the invention may be presented in the form of so-called claims. This is given below.

1. A *Bifidobacterium animalis* subsp. *lactis* strain containing an inactivated tetW on its chromosome obtainable by the process comprising the steps of:
    a. subjecting a culture of *Bifidobacterium animalis* subsp. *lactis* strain BB-12® cells, comprising a functional tetW on its chromosome and having a Minimum Inhibitive Concentration (MIC) of 4 microgram tetracycline/ml or higher, to a chemical mutagen which is ethidium bromide (EtBr),
    b. subjecting the cells to a physical mutagen which is ultra violet light (UV),
    c. transfer an aliquot of the UV treated culture to fresh medium containing a dose of tetracycline which is inhibitory to the growth of cells with an inactivated tetW, but tolerable to cells with a functional tetW,
    d. add a dose of penicillin or an analogue of penicillin (eg. ampicillin) which is detrimental to exponentially growing cells, but tolerable to non-growing cells, and continue to culture the cells,
    e. isolate cells that have acquired antibiotic sensitivity defined as having a MIC of 1.5 microgram tetracycline/ml or less,
    f. analyse the chromosomal tetW of said isolated, antibiotic sensitive cells, and
    g. select and expand antibiotic sensitive cells which is mutated in tetW,
wherein the mutated cell with an inactivated tetW is selected from the group consisting of the *Bifidobacterium animalis* subsp. *lactis* strains with the registration number DSM 18735 (CHCC 9870) or DSM 18776 (CHCC 9884) and a mutant strain, said mutant strain is obtained by using any of the deposited strains CHCC 9870 or CHCC 9884 as starting material and said mutant strain have a MIC of 1.5 microgram tetracycline/ml or less.

2. The *Bifidobacterium animalis* subsp. *lactis* strain according to claim 1, wherein cells that have a MIC of 1.0 microgram tetracycline/ml or less.

3. The *Bifidobacterium animalis* subsp. *lactis* strain according to any of the preceding claims, wherein the tetW gene comprise at least one sequence selected from the group of SEQ ID NO.:NO:3 [GAA AAT ACA AGC] and SEQ ID NO.:6 [GAA TAC AGG CTT]

4. A starter culture composition comprising the lactic acid bacterium according to any of the preceding claims, preferably wherein the starter culture composition is having a concentration of viable cells, which is in the range of $10^4$ to $10^{12}$ CFU per gram of the composition.

5. The starter culture composition according to claim 4, which in addition comprises one or more cryoprotective agent(s) selected from the group consisting of inosine-5' monophosphate (IMP), adenosine-5'-monophosphate (AMP), guanosine-5' monophosphate (GMP), uranosine-5'-monophosphate (UMP), cytidine-5' monophosphate (CMP), adenine, guanine, uracil, cytosine, adenosine, guanosine, uridine, cytidine, hypoxanthine, xanthine, hypoxanthine, orotidine, thymidine, inosine and a derivative of any of such compounds.

6. A method of manufacturing a food or feed product comprising adding a starter culture composition according to claim 4 or 5 to a food or feed product starting material and keeping the thus inoculated starting material under conditions where the lactic acid bacterium is metabolically active.

7. The method of claim 6, wherein the fermented food or feed product is a fermented dairy product.

8. The method of claim 7, wherein the fermented dairy product is a fermented dairy product selected from the list consisting of a fermented milk, a yoghurt, a cheese including a fresh cheese products or mozzarella, and buttermilk.

9. Use of a *Bifidobacterium animalis* subsp. *lactis* strain according to any of claims 1 to 3 for the preparation of an ingestible material or a bacterial culture.

10. The use according to claim 9, wherein the ingestible material comprises *Bifidobacteria* in an amount from about $10^5$ cfu/g to about $10^{12}$ cfu/g ingestible material.

11. The use according to any of the claim 9 or 10, wherein the ingestible material is a composition selected from the group consisting of milk, curd, milk based fermented products, acidified milk, yoghurt, frozen yoghurt, milk powder, milk based powders, milk concentrate, cheese, cheese spreads, dressings, beverages, ice creams, fermented cereal based products, infant formulae, and soybean milk.

12. The use according to any of the claims 9 to 11, wherein the ingestible material is used for the preparation of a composition for the treatment and/or prevention of a disease, syndrome or condition, or for improving digestion of nutrients, or for improving the general health status of a human being or a vertebrate animal.

13. The use according to any of the claims 9 to 12, wherein the ingestible material is used as a probiotic.

14. The use according to claims 9 to 13, wherein the ingestible material is a composition selected from the group consisting of milk, curd, milk based fermented products, acidified milk, yoghurt, frozen yoghurt, milk powder, milk based powders, milk concentrate, cheese, cheese spreads, dressings, beverages, ice creams, fermented cereal based products, infant formulae, tablets, capsules, liquid bacterial suspensions, dried oral supplement, wet oral supplement, dry tube feeding, or wet tube feeding.

15. The use according to any of claims 9 to 14, wherein the ingestible material is suitable for preventing or treating infections with pathogens.

16. A food or feed product comprising the bacterial cell of any of claims 1 to 3.

17. The use of the bacterial cell of any of claims 1 to 3 for the manufacture of a medicament.

EXAMPLES

Example 1

Inactivation of the tetW Gene in Two Probiotic Strains of *Bifidobacterium animalis* Subsp. *lactis* Expressing Resistance to Tetracycline A strong and dual mutagenic approach was used to inactivate the intrinsic tetracycline resistance of the genome of *Bifidobacterium animalis* subsp. *lactis* strain BB-12®. This included treatment of the cells with the mutagen, ethidium bromide (EtBr) followed by ultra violet radiation in a more forceful scale than normally when the mutagens are used individually.

Strains and Culture Conditions.

The strain *Bifidobacterium animalis* subsp. *lactis* BB-12° was obtained from the culture collection of Chr. Hansen A/S, Hørsholm, Denmark. *B. animalis* subsp. *lactis* strain 66-12® has the accession number CHCC5445 in the Hansen culture collection, and is deposited with the Deutsche Sammlung von Mikroorganismen un Zellkulturen (DSMZ) under accession number DSM15954.

The strain that is resistant to tetracycline (at least 15 microgram/ml, as determined by the E-test procedure, Danielsen and Wind, 2003), was grown routinely under anaerobically conditions at 37° C. in Difco-MRS broth (deMan, 1960), supplied with 0.05% Cysteine hydrochloride (Cysteine-HCl, Merck chemicals) as well as on MRS agar (1.5% agar) with the same concentration of Cysteine-HCl and 15 microgram of tetracycline per ml.

Mutagenic Treatment of BB-12

An aliquot (2%) of a BB-12® grown over night (on) in MRS was transferred to fresh MRS broth (10 ml without tetracycline) and incubated to optical density [OD] at 600 nm, 0.24 at which time the culture was supplied with EtBr to a final concentration of 1 microgram/ml and placed at room temperature (25° C.) for 30 min. The exponentially growing cells were then subjected to UV-radiation (UV cross-linker, Stratagene) in an open Petri dish for 10 min (70 mJ/cm$^2$). The UV treatment was repeated once after a dark interval of 5 min at room temperature. The treatment was adjusted to obtain a lethality of approximately 95%. The lethality was assessed as follows: The viability of the cells immediately after the EtBr-UV treatments was determined by cell plating on MRS agar without tetracycline and the lethality was calculated from the observed CFU.

One ml of the mutagenized culture was then transferred to 9 ml fresh MRS without the addition of EtBr and were then allowed to grow for a period of 16 hours at 37° C. in complete darkness, at which point aliquots of the treated cells were re-inoculated (1% [vol/vol]) into fresh MRS broth and allowed to grow for an additional 16 hours.

Example 2

Selection of Tetracycline-Sensitive Variants of Two Probiotic Isolates of *Bifidobacterium animalis* Subsp. *lactis*

Screening Procedure

Screening for tetracycline sensitive isolates was performed after an ampicillin enrichment procedure (Miller, 1972) adapted to Bifidobacteriacea. Briefly, the ampicillin enrichment procedure was performed by transferring an aliquot (1%) of the out-grown mutagenized culture to fresh MRS medium (10 ml) and growing the cells to an OD600 of 0.2 without the addition of tetracycline. 0.5 ml of this culture was used to inoculate 10 ml of MRS broth containing 10 microgram tetracycline/ml and incubated for 2 hrs at 37° C. at reduced oxygen tension—after which ampicillin was added to a final concentration of 150 microgram/ml, and the culture was continuously incubated for 16 hrs at 37° C. As ampicillin kills only growing cells (i.e., TetR cells) and not non-dividing cells (i.e. mutant TetS cells), the addition of ampicillin can be considered an enrichment step for the subsequent isolation of TetS mutants. Cells were harvested by centrifugation (4,000×G for 5 min at 4° C.) and rinsed twice with fresh MRS broth.

Following the ampicillin enrichment the screening for tetracycline sensitive isolates was performed by plating aliquots of the washed cells on MRS agar in an appropriate dilution to give approximately 150-200 colonies per plate after incubation at 37° C. for 40 hours.

Tetracycline sensitive colonies were identified by replica plating on MRS agar without antibiotics and MRS agar containing 5 microgram of tetracycline per ml, on which the tetracycline sensitive isolates were unable to grow. Finally, the tetracycline sensitive colonies were cultured in MRS broth. Total genomic DNA was isolated from the tetracycline sensitive clones and the tetracycline resistant strain for intensive characterization. The replica screening resulted in 2 tetracycline sensitive isolates from CHCC5445 of a total of approximately 1,400 screened colonies. The colonies were further tested in liquid MRS broth containing tetracycline (5 microgram/ml). Both isolates did not manage to grow under these conditions and were then subjected to E-test susceptibility screening to determine their tetracycline sensitive threshold.

The E-test was performed according to the method of the manufacturer (AB BIODISK, Sweden),—slightly modified by M. Danielsen and A. Wind (2003). Briefly, determination of the Minimum Inhibitory Concentration (MIC) value for the individual isolates was performed by dipping a sterile cotton swab into an overnight culture of the tetracycline sensitive strain to be tested and to streak the entire surface of a MRS agar plate (diameter: 8.5 cm) evenly in three directions. After dryness of the applied inoculum an E-test strip was applied to the agar surface by help of a manual applicator with the MIC scale facing upwards. Plates were inoculated anaerobically in an inverted position at 37° C. over night. The MIC value was determined by reading the value where the edge of the inhibition ellipse intersects the strip. In both cases the two isolates, named Bb12Tet-S70 and Bb12Tet-S705, demonstrated sensitivity to tetracycline with a MIC value of 0.5 microgram/ml.

Example 3

Molecular Characterization of the Two Tetracycline-Sensitive Derivatives of the Probiotic Strain *Bifidobacterium animalis* Subsp. *lactis*

PCR Amplification and DNA Sequencing of the tetW Gene.

Genomic DNA was prepared from wild type BB-12® and the two tetracycline-sensitive isolates by the use of the Easy-DNA protocol for isolation of DNA from gram-positive bacteria according to the manufacturer's (Qiagen) instructions. The tetW gene of the sensitive variants was characterized by PCR analyses according to the protocol of Innis and Gelfand (1990), and DNA sequencing to test for possible mutations in that gene. The entire open reading frame (ORF, approx. 2.0 kb) of tetW was amplified from each isolate in three overlapping fragments (A, B and C) with three sets of primers (table 1, table 2).

The amplified fragments from the three PCR reactions were subjected to agarose gel-electrophoresis (0.7%) and staining in EtBr and identified with UV illumination. The bands corresponding to the three amplified gene fragments were excised from the gel and DNA was extracted (QIAquick gel extraction kit from Qiagen) The purified PCR products were cloned into the plasmid vector, pCR2.1-TOPO (Invitrogen), for nucleotide sequence determination using the M13 forward and reverse primers. DNA sequencing was also performed directly on the amplified PCR fragments using the amplification primers and sequencing primers (table 1).

Sequencing of the tetW genes from the two isolates with tetracycline E-test-values of 0.5 microgram tetracycline/ml showed that in both cases the tetW gene was affected. The Bb12Tet-S70 demonstrated a frame-shift at nucleotide position #1515, where an adenine residue was deleted as illustrated below and in table 2.

```
Amino acid sequence:
Glu Lys Tyr Lys Leu Glu Thr Val Val Lys

Bb12 ® nt # 1510:
gaa aaa tac aag ctt gaa aca gtg gta aag

Bb12tet-S70 nt #1510:
gaa aat aca agc ttg aaa cag tgg taa

Amino acid sequence:
Glu Asn Thr Ser Leu Lys Gln Trp Ochre stop
```

The illustration above shows a partial sequence of the tetW gene in CHCC5445. The underlined adenine residue in BB-12® (nt: 1515 in the tetW sequence SEQ ID NO.:16) is deleted in the frame-shift mutant, Bb12Tet-S70, resulting in an ochre stop/nonsense codon 205 amino acids short of the wild type tetW gene product.

DNA sequencing of the tetW gene from the other tetracycline sensitive isolate, Bb12Tet-S705 (CHCC9884; DSM 18776), demonstrated a transition of a guanine to an adenine residue at nucleotide position #1807 generating a missense mutation (Glycine to Arginine) as depicted in table 2.

Example 4

Genetic Stability of the Tetracycline Sensitive Isolates Bb12Tet-S70 (CHCC9870) and Bb12Tet-S705 (CHCC9884)

Determination of back mutation rates by cell plating on MRS agar with tetracycline. One ml of a culture of the Bb12Tet-S70 mutant strain ($4.8 \times 10^9$ cells/all) grown over night was spread with 100 ml each onto 10 Petri dishes (diameter: 13.8 cm) with MRS agar supplied with tetracycline (10 microgram/ml). After 48 hours of anaerobic incubation at 37° C., 4 colonies could be detected on the plates demonstrating that the reversion rate is $0.8 \times 10^{-9}$.

The stability testing was performed for the Bb12Tet-S705 strain as well. An over night culture of this strain ($1.3 \times 10^9$ cells/ml) was likewise spread with 100 ml each onto 10 Petri dishes with MRS agar supplied with tetracycline (10 microgram/ml). After the incubation period 8 tetracycline resistant colonies were detected. The reversion rate for the missense mutation was calculated to $6.1 \times 10^{-9}$.

Example 5

Physiological and Phenotypic Testings of the Two Tetracycline Sensitive Strains, Bb12Tet-S70 (CHCC9870) and Bb12Tet-S705 (CHCC9884)

Growth Conditions of the Mutant Strains in MRS Broth.

Growth of the Bb12Tet-S70 and Bb12Tet-S705 was compared to their mother strain, CHCC5445, grown under similar conditions in MRS broth (200 ml with Cysteine-HCl) over a period of 24 hours. Samples for measuring the optical density at 600 was monitored along the incubation period. The growth rates for both mutants were similar to that of the parent wild type strain indicating that the mutagenic treatment of the tetracycline sensitive isolates did not seem to hamper genes in their fermentative pathways.

DNA-Fingerprinting Analysis.

Pulsed-field gel-electrophoresis of the genomic SpeI and XbaI-digested DNA from the two tetW mutant strains was performed according to standard methods (Hung and Bandziulis, 1990), and did not reveal any rearrangement of the SpeI- or XbaI-digested chromosomal pattern when compared to the respective wild type strain. This adds evidence to an overall isogenic background of the mutants and the mother strain.

REFERENCES

1. Barbosa, T. M., K. P. Scott, and H. J. Flint. (1999). Evidence for recent intergeneric transfer of a new tetracycline resistance gene, tet(W), isolated from *Butyrivibrio fibrisolvens*, and the occurrence of tet(O) in ruminal bacteria. Environ. Microbiol. 1:53-64.
2. Billington, S. J, J. G. Songer, and B. H. Jost (2002) Widespread Distribution of a Tet W Determinant among Tetracycline-Resistant Isolates of the Animal Pathogen Arcanobac-terium pyogenes. ANTIMICROBIAL AGENTS AND CHEMOTHERAPY, 46:1281-1287.
3. Chopra, I., and M. Roberts. (2001). Tetracycline antibiotics: mode of action, applications, molecular biology, and epidemiology of bacterial resistance. Microbiol. Mol. Biol. Rev. 65:232-260.
4. de Man, J. C., M. Rogosa, and M. E. Sharpe. (1960). A medium for the cultivation of lactobacilli. J. Appl. Bacteriol. 23:130-135.
5. Lachman, L. et al (Ed.) (1986). The Theory and Practice of Industrial Pharmacy. Third Edition. Lea & Febiger, Philadelphia.
6. EP157 071
7. P 768 375 (Nestle S A), 12 Jun. 2002.
8. FSA (2005) Opinion of the Scientific Panel on Additives and Products or Substances used in Animal Feed on the updating of the criteria used in the assessment of bacteria for resistance to antibiotics of human or veterinary importance (Question N° EFSA-Q2004-079) The EFSA Journal 223, 1-12. (http://www.efsa.eu.intlscience/feedap/feedapopinions/993en.html)
9. WHO (2002). Joint FAO/WHO Working Group Report on Guidelines for the Evaluation of Probiotics in Food. London Ontario. Apr. 30-May 1, 2002. (http://www.fao.org/es/esn/Probio/wgreport2.pdf)
10. Danielsen and A. Wind. (2003) "Susceptibility of *Lactobacillus* spp. to antimicrobial agents". Int. J. Food Microbiol. 82:1-11.
11. Innis, M. A. and D. H. Gelfand (1990) (Optimization of PCRs, p. 3-12. In M. A. Innis, D. H. Gelfand, J. J. Sninsky, and T. J. White (ed), PCR protocols, a guide to methods and applications. Academic Press, San Diego, Calif.),
12. Hung, L. and R. Bandziulis, Promega Notes 24:1-2, (1990), Promega, Madison, Wis.
13. Laulund, S. (1994). Commercial aspects of formulation, production and marketing of probiotic products. IN: Human Health: The contribution of microorganisms. pp. 158-173. Gibson, S. A. W. (Ed.). Springer-Verlag, London.
14. Masco et al (2004) Int. J. Syst. Evol Microbiol 54, 1137-1143
15. Miller, J. H. (1972) "Experiments in molecular genetics", p 230-234. Cold Spring Harbor Laboratory, Cold Spring Harbor, N.Y.
16. SCAN (2003) EUROPEAN COMMISSION's Scientific Committee on Animal Nutrition (SCAN) on the Criteria for Assessing the Safety of Micro-Organisms Resistant to Antibiotics of Human Clinical and Veterinary of 3 Jul. 2001, revised on 24 Jan. 2003.
17. U.S. Pat. No. 6,379,663 (New Zealand Dairy Board), 30 Apr. 2002
18. WO 01/97822 (Aboatech O Y), 27 Dec. 2001
19. WO 03/099037 (Nestec S A), 4 Dec. 2004
20. Zhou, J. S., C. J. Pillidge C, P. K. Gopal and H. S. Gill (2005) Antibiotic susceptibility pro-files of new probiotic *Lactobacillus* and *Bifidobacterium* strains. International Journal of Food Microbiology 98:211-217.
21. Yazid, A. M., A. M. Ali, M. Shuhaimi, V. Kalaivaani, M. Y. Rokiah and A. Reezal (2000) Antimicrobial susceptibility of *Bifidobacteria*. Letters in Applied Microbiology 2000, 31, 57-62

REGARDING DEPOSITED MICROBIAL ORGANISMS

Expert Solution

For all deposited microbial organisms mentioned in the present patent application the following applies.

In respect to those designations in which a European Patent is sought a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies. (Rule 28 (4) and 28 (5) EPC).

Tables

TABLE 1

Oligonucleotides used for PCR analyses and DNA sequencing of the tetracycline resistance-encoding tetW mutants.

| Primer | Sequence (5' to 3') | Nucleotide positions* |
|---|---|---|
| SET A: | | |
| tetW x.D1 | CGGCACCTGCTGTATAATGCGGATTGTGGC | 2:31 |
| tetW x.D0 (seq.) | GCCCTTCGGGGCAGTAAAGGGAGG | 266:289 |
| tetW x.R2 | GCAGACGGTGTCGCTGTCCCCGG | 762:784 |
| SET B: | | |
| tetW x.D4 | GGCTGGCGTTGATTTGCAGAGCGTGG | 693:718 |
| tetW A.D5 (seq.) | GGGGAGCGCCGCCCTATGCGGC | 1029:1050 |
| tetW x.R5 | CGAGGTGCCGCCCAACCCGTTTTGGGC | 2599:1625 |
| SET C: | | |
| tetW x.D3 | GGAGCGGCCGCTCAAAGCAGCCAGCC | 1560:1581 |
| tetW x.R6 (seq.) | GCGAGGAAGGTTATTGCATTTCCC | +10:+33 |
| tetW x.R4 | GGGAGTGACCCCGCCGATCATGCGACCATC | +233:+262 |

(seq.): primers used only for DNA sequencing.
*Numbering is based on the DNA sequence illustrated in table 2.
+nt position downstream of the translational stop codon, Opal (not illustrated in table 2) (Opal nt postion 2215 in table 2).
The prefix "D" indicates a direct primer derived from the sense strand. The prefix "R" indicates a reverse primer complementary to the sense strand.

TABLE 2

The tetW DNA sequence flanked by the upstream transposase
gene, tps, from *Bifidobacterium animalis* subsp. *lactis* BB-12
(SEQ ID NO.: 16).

```
TCGGCACCTGCTGTATAATGCGGATTGTGGCATTTGTGCGGTGTTGCCTTAAATAAAACT
                                                                    60
AGCCGTGGACGACATATTACGCCTAACACCGTAAACACGCCACAACGGAATTTATTTTGA

ATAATCAAATAGTGGGAACAAAGGATTATGATAGTCCCTTTTGTAGGGGCTTAGTTTTTT
                                                                   120
TATTAGTTTATCACCCTTGTTTCCTAATACTATCAGGGAAAACATCCCCGAATCAAAAAA

GTACCCAATTTAAGAATACTTTTGCCTTATCAATTTTGACATATCCCCAAAAACAGCACT
                                                                   180
CATGGGTTAAATTCTTATGAAAACGGAATAGTTAAAACTGTATAGGGGTTTTTGTCGTGA

CACAAACAGGTGTATGCTGTATATGTGTATGTCCGCAAATTATCATCCCCAGTGGTAAAA
                                                                   240
GTGTTTGTCCACATACGACATATACACATACAGGCGTTTAATAGTAGGGGTCACCATTTT

Tetracycline Start
GTATTTTACTGCTGGGGATTTTTATGCCCTTCGGGGCAGTAAAGGGAGGACAATCACATG
                                                                   300
CATAAAATGACGACCCCTAAAAATACGGGAAGCCCCGTCATTTCCCTCCTGTTAGTGTAC
                                                                M AAAATAATCAATATTGGAATTCTTGCCCATGTAGACGCTGGAAAGACGACCTTGACGGAG
                                                                   360
TTTTATTAGTTATAACCTTAAGAACGGGTACATCTGCGACCTTTCTGCTGGAACTGCCTC
  K  I  I  N  I  G  I  L  A  H  V  D  A  G  K  T  T  L  T  E AGCCTGCTATATGCCAGCGGAGCCATTTCAGAACCGGGGAGCGTCGAAAAAGGGACAACG
                                                                   420
TCGGACGATATACGGTCGCCTCGGTAAAGTCTTGGCCCCTCGCAGCTTTTTCCCTGTTGC
  S  L  L  Y  A  S  G  A  I  S  E  P  G  S  V  E  K  G  T  T AGGACGGACACCATGCTTTTGGAGCGGCAGCGTGGGATTACCATTCAAGCGGCAGTCACT
                                                                   480
TCCTGCCTGTGGTACGAAAACCTCGCCGTCGCACCCTAATGGTAAGTTCGCCGTCAGTGA
  R  T  D  T  M  L  L  E  R  Q  R  G  I  T  I  Q  A  A  V  T TCCTTCCAGTGGCACAGATGTAAAGTCAACATTGTGGATACGCCCGGCCACATGGATTTT
                                                                   540
AGGAAGGTCACCGTGTCTACATTTCAGTTGTAACACCTATGCGGGCCGGTGTACCTAAAA
  S  F  Q  W  H  R  C  K  V  N  I  V  D  T  P  G  H  M  D  F TTGGCGGAGGTGTACCGCTCTTTGGCTGTTTTAGATGGGGCCATCTTGGTGATCTCCGCT
                                                                   600
AACCGCCTCCACATGGCGAGAAACCGACAAAATCTACCCCGGTAGAACCACTAGAGGCGA
  L  A  E  V  Y  R  S  L  A  V  L  D  G  A  I  L  V  I  S  A AAAGATGGCGTGCAGGCCCAGACCCGTATTCTGTTCCATGCCCTGCGGAAAATGAACATT
                                                                   660
TTTCTACCGCACGTCCGGGTCTGGGCATAAGACAAGGTACGGGACGCCTTTTACTTGTAA
  K  D  G  V  Q  A  Q  T  R  I  L  F  H  A  L  R  K  M  N  I CCCACCGTTATCTTTATCAACAAGATCGACCAGGCTGGCGTTGATTTGCAGAGCGTGGTT
                                                                   720
GGGTGGCAATAGAAATAGTTGTTCTAGCTGGTCCGACCGCAACTAAACGTCTCGCACCAA
  P  T  V  I  F  I  N  K  I  D  Q  A  G  V  D  L  Q  S  V  V CAGTCTGTTCGGGATAAGCTCTCCGCCGATATTATCATCAAGCAGACGGTGTCGCTGTCC
                                                                   780
GTCAGACAAGCCCTATTCGAGAGGCGGCTATAATAGTAGTTCGTCTGCCACAGCGACAGG
  Q  S  V  R  D  K  L  S  A  D  I  I  I  K  Q  T  V  S  L  S CCGGAAATAGTCCTGGAGGAAAATACCGACATAGAAGCATGGGATGCGGTCATCGAAAAT
                                                                   840
GGCCTTTATCAGGACCTCCTTTTATGGCTGTATCTTCGTACCCTACGCCAGTAGCTTTTA
  P  E  I  V  L  E  E  N  T  D  I  E  A  W  D  A  V  I  E  N AACGATAAATTATTGGAAAAGTATATCGCAGGAGAACCAATCAGCCGGGAAAAACTTGTG
                                                                   900
TTGCTATTTAATAACCTTTTCATATAGCGTCCTCTTGGTTAGTCGGCCCTTTTTGAACAC
  N  D  K  L  L  E  K  Y  I  A  G  E  P  I  S  R  E  K  L  V CGGGAGGAACAGCGGCGGGTTCAAGACGCCTCCCTGTTCCCGGTCTATTATGGCAGCGCC
                                                                   960
GCCCTCCTTGTCGCCGCCCAAGTTCTGCGGAGGGACAAGGGCCAGATAATACCGTCGCGG
  R  E  E  Q  R  R  V  Q  D  A  S  L  F  P  V  Y  Y  G  S  A
```

TABLE 2-continued

The tetW DNA sequence flanked by the upstream transposase
gene, tps, from *Bifidobacterium animalis* subsp. *lactis* BB-12
(SEQ ID NO.: 16).

```
AAAAAGGGCCTTGGCATTCAACCGTTGATGGATGCGGTGACAGGGCTGTTCCAACCGATT
------------------------------------------------------------  1020
TTTTTCCCGGAACCGTAAGTTGGCAACTACCTACGCCACTGTCCCGACAAGGTTGGCTAA
 K  K  G  L  G  I  Q  P  L  M  D  A  V  T  G  L  F  Q  P  I

GGGGAACAGGGGAGCGCCGCCCTATGCGGCAGCGTTTTCAAGGTGGAGTATACAGATTGC
------------------------------------------------------------  1080
CCCCTTGTCCCCTCGCGGCGGGATACGCCGTCGCAAAAGTTCCACCTCATATGTCTAACG
 G  E  Q  G  S  A  A  L  C  G  S  V  F  K  V  E  Y  T  D  C

GGCCAGCGGCGTGTCTATCTACGGCTATACAGCGGAACGCTGCGCCTGCGGGATACGGTG
------------------------------------------------------------  1140
CCGGTCGCCGCACAGATAGATGCCGATATGTCGCCTTGCGACGCGGACGCCCTATGCCAC
 G  Q  R  R  V  Y  L  R  L  Y  S  G  T  L  R  L  R  D  T  V

GCCCTGGCCGGGAGAGAAAAGCTGAAAATCACAGAGATGCGTATTCCATCCAAAGGGGAA
------------------------------------------------------------  1200
CGGGACCGGCCCTCTCTTTTCGACTTTTAGTGTCTCTACGCATAAGGTAGGTTTCCCCTT
 A  L  A  G  R  E  K  L  K  I  T  E  M  R  I  P  S  K  G  E

ATTGTTCGGACAGACACCGCTTATCCGGGTGAAATTGTTATCCTTCCCAGCGACAGCGTG
------------------------------------------------------------  1260
TAACAAGCCTGTCTGTGGCGAATAGGCCCACTTTAACAATAGGAAGGGTCGCTGTCGCAC
 I  V  R  T  D  T  A  Y  P  G  E  I  V  I  L  P  S  D  S  V

AGGTTAAACGATGTATTAGGGGACCCCAACCCGGCTCCCTCGTAAAAGGTGGCGTGAGGAC
------------------------------------------------------------  1320
TCCAATTTGCTACATAATCCCCTGGGTTGGGCCGAGGGAGCATTTTCCACCGCACTCCTG
 R  L  N  D  V  L  G  D  P  T  R  L  P  R  K  R  W  R  E  D

CCCCTCCCCATGCTGCGGACGTCGATTGCGCCGAAAACGGCAGCGCAAAGAGAACGGCTG
------------------------------------------------------------  1380
GGGGAGGGGTACGACGCCTGCAGCTAACGCGGCTTTTGCCGTCGCGTTTCTCTTGCCGAC
 P  L  P  M  L  R  T  S  I  A  P  K  T  A  A  Q  R  E  R  L

CTGGACGCTCTTACGCAACTTGCGGATACTGACCCGCTTTTGCGCTGCGAGGTGGATTCC
------------------------------------------------------------  1440
GACCTGCGAGAATGCGTTGAACGCCTATGACTGGGCGAAAACGCGACGCTCCACCTAAGG
 L  D  A  L  T  Q  L  A  D  T  D  P  L  L  R  C  E  V  D  S

ATCACCCATGAGATCATTCTTTCTTTTTTGGGCCGGGTGCAGTTGGAGGTTGTTTCCGCT
------------------------------------------------------------  1500
TAGTGGGTACTCTAGTAAGAAAGAAAAAACCCGGCCCACGTCAACCTCCAACAAAGGCGA
 I  T  H  E  I  I  L  S  F  L  G  R  V  Q  L  E  V  V  S  A

#1515 Bb12Tet-S70 (deletion of A #1515)
TTGCTGTCGGAAAAATACAAGCTTGAAACAGTGGTAAAGGAACCCACCGTCATTTATATG
------------------------------------------------------------  1560
AACGACAGCCTTTTTATGTTCGAACTTTGTCACCATTTCCTTGGGTGGCAGTAAATATAC
 L  L  S  E  K  Y  K  L  E  T  V  V  K  E  P  T  V  I  Y  M GAGCGGCCGCTCAAAGCAGCCAGCCACACCATCCATATCGAGGTGCCGCCCAACCCGTTT
------------------------------------------------------------  1620
CTCGCCGGCGAGTTTCGTCGGTCGGTGTGGTAGGTATAGCTCCACGCGGGTTGGGCAAA
 E  R  P  L  K  A  A  S  H  T  I  H  I  E  V  P  P  N  P  F TGGGCATCCATCGGACTGTCTGTTACACCACTCCCGCTTGGCTCCGGTGTACAATACAAG
------------------------------------------------------------  1680
ACCCGTAGGTAGCCTGACAGACAATGTGGTGAGGGCGAACCGAGGCCACATGTTATGTTC
 W  A  S  I  G  L  S  V  T  P  L  P  L  G  S  G  V  Q  Y  K AGCCGGGTTTCGCTGGGATACTTGAACCAGAGTTTTCAAAACGCTGTCAGGGATGGTATC
------------------------------------------------------------  1740
TCGGCCCAAAGCGACCCTATGAACTTGGTCTCAAAAGTTTTGCGACAGTCCCTACCATAG
 S  R  V  S  L  G  Y  L  N  Q  S  F  Q  N  A  V  R  D  G  I CGTTACGGGCTGGAGCAGGGCTTGTTCGGCTGGAACGTAACGGACTGTAAGATTTGCTTT
------------------------------------------------------------  1800
GCAATGCCCGACCTCGTCCCGAACAAGCCGACCTTGCATTGCCTGACATTCTAAACGAAA
 R  Y  G  L  E  Q  G  L  F  G  W  N  V  T  D  C  K  I  C  F
```

TABLE 2-continued

The tetW DNA sequence flanked by the upstream transposase gene, tps, from *Bifidobacterium animalis* subsp. *lactis* BB-12 (SEQ ID NO.: 16).

```
                    #1807 Bb12Tet-705 (G -> A in position #1807)
GAATACGGGCTTTATTACAGTCCGGTCAGCACGCCGGCGGACTTCCGCTCATTGGCCCCG
------------------------------------------------------------ 1860
CTTATGCCCGAAATAATGTCAGGCCAGTCGTGCGGCCGCCTGAAGGCGAGTAACCGGGGC
 E   Y   G   L   Y   Y   S   P   V   S   T   P   A   D   F   R   S   L   A   P ATTGTATTGGAACAGGCATTGAAGGAATCAGGGACGCAACTGCTGGAACCTTATCTCTCC
------------------------------------------------------------ 1920
TAACATAACCTTGTCCGTAACTTCCTTAGTCCCTGCGTTGACGACCTTGGAATAGAGAGG
 I   V   L   E   Q   A   L   K   E   S   G   T   Q   L   L   E   P   Y   L   S TTCACCCTCTATGCGCCCCGGGAATATCTTTCCAGGGCTTATCATGATGCACCGAAATAC
------------------------------------------------------------ 1980
AAGTGGGAGATACGCGGGGCCCTTATAGAAAGGTCCCGAATAGTACTACGTGGCTTTATG
 F   T   L   Y   A   P   R   E   Y   L   S   R   A   Y   H   D   A   P   K   Y TGTGCCACCATCGAAACGGTCCAGGTAAAAAAGGATGAAGTTGTCTTTACTGGCGAGATT
------------------------------------------------------------ 2040
ACACGGTGGTAGCTTTGCCAGGTCCATTTTTTCCTACTTCAACAGAAATGACCGCTCTAA
 C   A   T   I   E   T   V   Q   V   K   K   D   E   V   V   F   T   G   E   I CCCGCCCGCTGTATACAGGCATACCGTACTGATCTGGCCTTTTACACCAACGGGCAGAGC
------------------------------------------------------------ 2100
GGGCGGGCGACATATGTCCGTATGGCATGACTAGACCGGAAAATGTGGTTGCCCGTCTCG
 P   A   R   C   I   Q   A   Y   R   T   D   L   A   F   Y   T   N   G   Q   S GTATGCCTTACAGAACTGAAAGGGTATCAGGCCGCTGTCGGCAAGCCAGTCATCCAGCCC
------------------------------------------------------------ 2160
CATACGGAATGTCTTGACTTTCCCATAGTCCGGCGACAGCCGTTCGGTCAGTAGGTCGGG
 V   C   L   T   E   L   K   G   Y   Q   A   A   V   G   K   P   V   I   Q   P Tetracycline Stop
CGCCGTCCAAACAGCCGCCTGGACAAGGTGCGCCATATGTTCAGTAAGATCACTTGATAC
------------------------------------------------------------ 2220
GCGGCAGGTTTGTCGGCGGACCTGTTCCACGCGGTATACAAGTCATTCTAGTGAACTATG
 R   R   P   N   S   R   L   D   K   V   R   H   M   F   S   K   I   T   *
```

Nucleotide sequence of the tetW gene from *Bifidobacterium animalis* subsp. *lactis* BB-12 ®. The sequence was obtained by sequencing at Chr. Hansen A/S.
The nucleotide (nt) sequence # 298-2217 is the tetracycline resistant encoding gene, tetW, with the amino acid outlined under the DNA sequence (M. W. approx. 70 kDa).
The start codon (ATG) is underlined.
The mutation in strain Bb12Tet-S70 (CHCC9870; DSM 18735), which comprises a frame-shift mutation at nt position #1515 is indicated above the DNA sequence, and underlined. The missense mutation (guanine to adenine) in strain Bb12Tet-S705 (CHCC9884; DSM 18776) at nt position # 1807 is likewise indicated in the DNA sequence.
*): indicates a stop codon, underlined.

---

The invention claimed is:

1. An isolated *Bifidobacterium animalis* subspecies *lactis* strain containing an inactivated tetW on its chromosome, wherein said strain is selected from the group consisting of:
   (i) the *Bifidobacterium animalis* subspecies *lactis* strains having the registration number DSM 18735 (CHCC 9870) or DSM 18776 (CHCC 9884), and
   (ii) a mutant strain which is obtained by using either of the deposited strains DSM 18735 (CHCC 9870) and DSM 18776 (CHCC 9884) as starting material and said mutant strain has a minimum inhibitory concentration of 1.5 microgram tetracycline/ml or less, wherein the tetW gene of said mutant comprises either the sequence of SEQ ID NO: 3 [GAA AAT ACA AGC] or the sequence of SEQ ID NO: 6 [GAA TAC AGG CTT].

2. A starter culture composition comprising the lactic acid bacterium according to claim 1, preferably wherein the starter culture composition is having a concentration of viable cells, which is in the range of $10^4$ to $10^{12}$ CFU per gram of the composition.

3. A food or feed product comprising the bacterial cell of claim 1.

* * * * *